US00PP19269P2

(12) United States Plant Patent
Catt

(10) Patent No.: US PP19,269 P2
(45) Date of Patent: Sep. 23, 2008

(54) ***CERATOSTIGMA* PLANT NAMED 'MY LOVE'**

(50) Latin Name: *Ceratostigma willmottianum*
Varietal Denomination: My Love

(76) Inventor: Peter Catt, Liss Forest Nursery Ltd, Petersfield Road, Greatham, Liss, Hants GU33 6HA (GB)

( * ) Notice: Subject to any disclaimer, the term of this patent is extended or adjusted under 35 U.S.C. 154(b) by 106 days.

(21) Appl. No.: 11/650,785

(22) Filed: Jan. 5, 2007

(51) Int. Cl.
*A01H 5/00* (2006.01)

(52) U.S. Cl. ..... Plt./226

(58) Field of Classification Search ..... Plt./226
See application file for complete search history.

(56) References Cited

U.S. PATENT DOCUMENTS

PP7,822 P * 3/1992 Scott ..... Plt./226
PP12,822 P2 * 8/2002 Moolenaar ..... Plt./226
PP13,953 P3 * 7/2003 Crocker ..... Plt./226

* cited by examiner

*Primary Examiner*—Wendy C. Haas

(57) ABSTRACT

A new cultivar of *Ceratostigma* named 'My Love' that is characterized by compact habit, intense golden-yellow foliage, and clear-blue flowers in summer. In combination these traits set 'My Love' apart from all other existing varieties of *Ceratostigma* known to the inventor.

2 Drawing Sheets

Genus: *Ceratostigma.*
Species: *willmottianum.*
Denomination: 'My Love'.

BACKGROUND OF THE INVENTION

The present invention relates to a new and distinct cultivar of plumbago, an ornamental plant suitable for use as a single species container plant or as a shrub for small gardens. The new cultivar is known botanically as *Ceratostigma willmottianum* and will be referred to hereinafter by the cultivar name 'My Love'.

The new *Ceratostigma* cultivar named 'My Love' is a seedling selection that resulted from a controlled breeding program initiated in 1989. Cross-pollination was conducted by the inventor using an individual *Ceratostigma willmottianum* 'Forest Blue' (unpatented) as the female parent, and an individual *Ceratostigma willmottianum* 'Desert Skies' (unpatented) as the male parent. The cross-pollination was accomplished at the inventor's nursery in Hampshire, United Kingdom. Both parents had been previously raised and introduced by the inventor.

Seed husks were collected in November 1999 from a plant of *Ceratostigma* 'Forest Blue'. Seed from the husks was sown the following February 2000 and the resulting seedlings were grown out. Three seedlings showing yellow leaves were isolated from the batch and grown on and the most compact form was selected and given the name of *Ceratostigma* 'My Love' based on the criteria of compact habit and intense golden-yellow foliage.

The female parent 'Forest Blue' exhibits compact habit, and the male parent 'Desert Skies' exhibits yellow foliage. In addition to being distinguishable from the female parent by foliage color 'My Love' is robust and more compact than the female parent. 'My Love' is distinguishable from the male parent by compact habit. The new *Ceratostigma* variety named 'My Love' exhibits compact habit, intense golden-yellow foliage, and clear blue flowers. Blooming is prolific and occurs in summer. Plant dimensions at maturity are 30 cm in height and 60 cm in width. 'My Love' is hardy to USDA Zone 7 and is deciduous. Cultural recommendations include full sun or part shade, moderate to regular water, and moderately fertile well-draining soil.

The new *Ceratostigma* cultivar 'My Love' was first asexually propagated by the inventor in Hampshire, United Kingdom. Asexual propagation was conducted in 2001 and the method used was semi-ripe stem cuttings. Since that time, under careful observation, the distinguishing characteristics have been determined stable, uniform, and reproduce true to type in successive generations of asexual propagation.

SUMMARY OF THE INVENTION

The following represent the distinguishing characteristics of the new *Ceratostigma* cultivar named 'My Love'. In combination these traits set 'My Love' apart from all other existing varieties of *Ceratostigma* known to the inventor. 'My Love' has not been tested under all possible conditions and phenotypic differences may be observed with variations in environmental, climatic, and cultural conditions, however, without any variance in genotype.

1. 'My Love' exhibits compact habit.
2. 'My Love' exhibits clear-blue flowers in summer.
3. 'My Love' exhibits intense golden-yellow foliage.
4. 'My Love' is winter deciduous.
5. 'My Love' is drought tolerant.
6. 'My Love' reaches 30 cm. in height and 60 cm. in width at maturity.
7. 'My Love' is hardy to USDA Zone 7.
8. 'My Love' is asexually propagated using the method of semi-ripe cuttings.

BRIEF DESCRIPTION OF THE DRAWINGS

The accompanying color drawings illustrate the overall appearance of the new *Ceratostigma* cultivar named 'My Love' showing the color as true as it is reasonably possible to obtain in color reproductions of this type. Color in the drawings may differ from the color values cited in the detailed botanical description, which accurately describe the actual color of the new variety 'My Love'.

The drawing labeled

The drawing labeled

Figure 1:
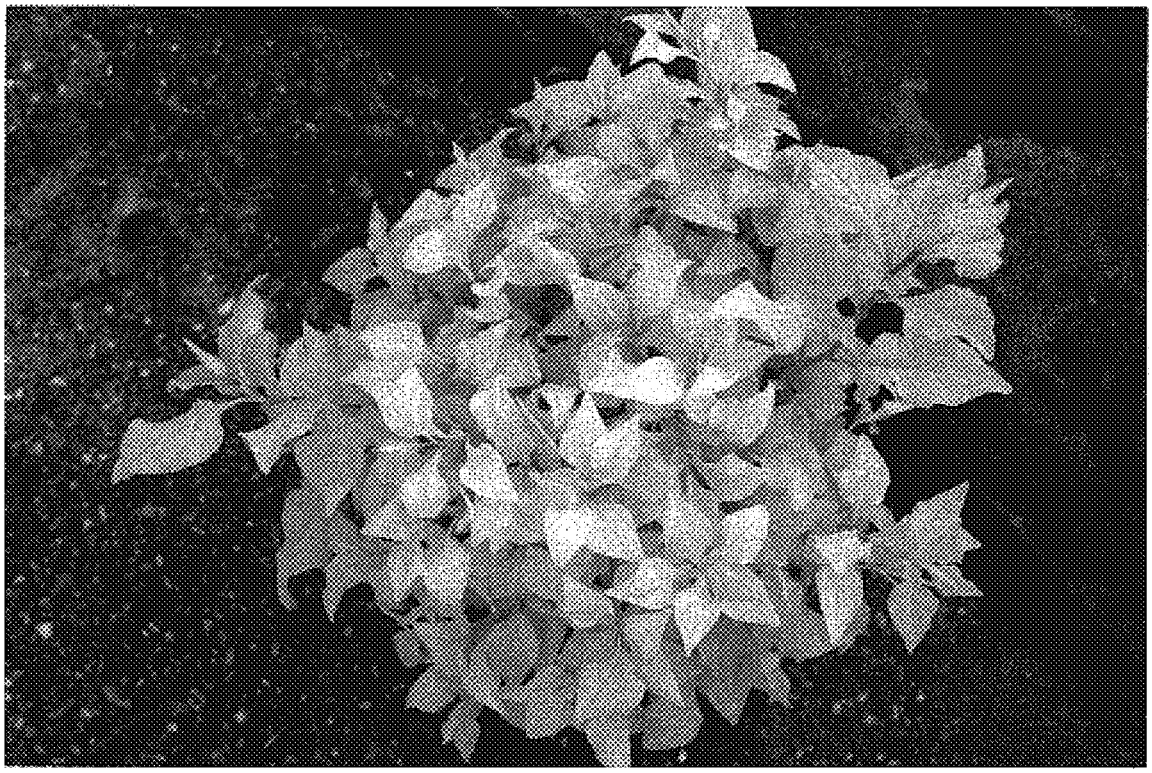
FIG. 1 depicts a side view of the plant illustrating habit.
Figure 2:
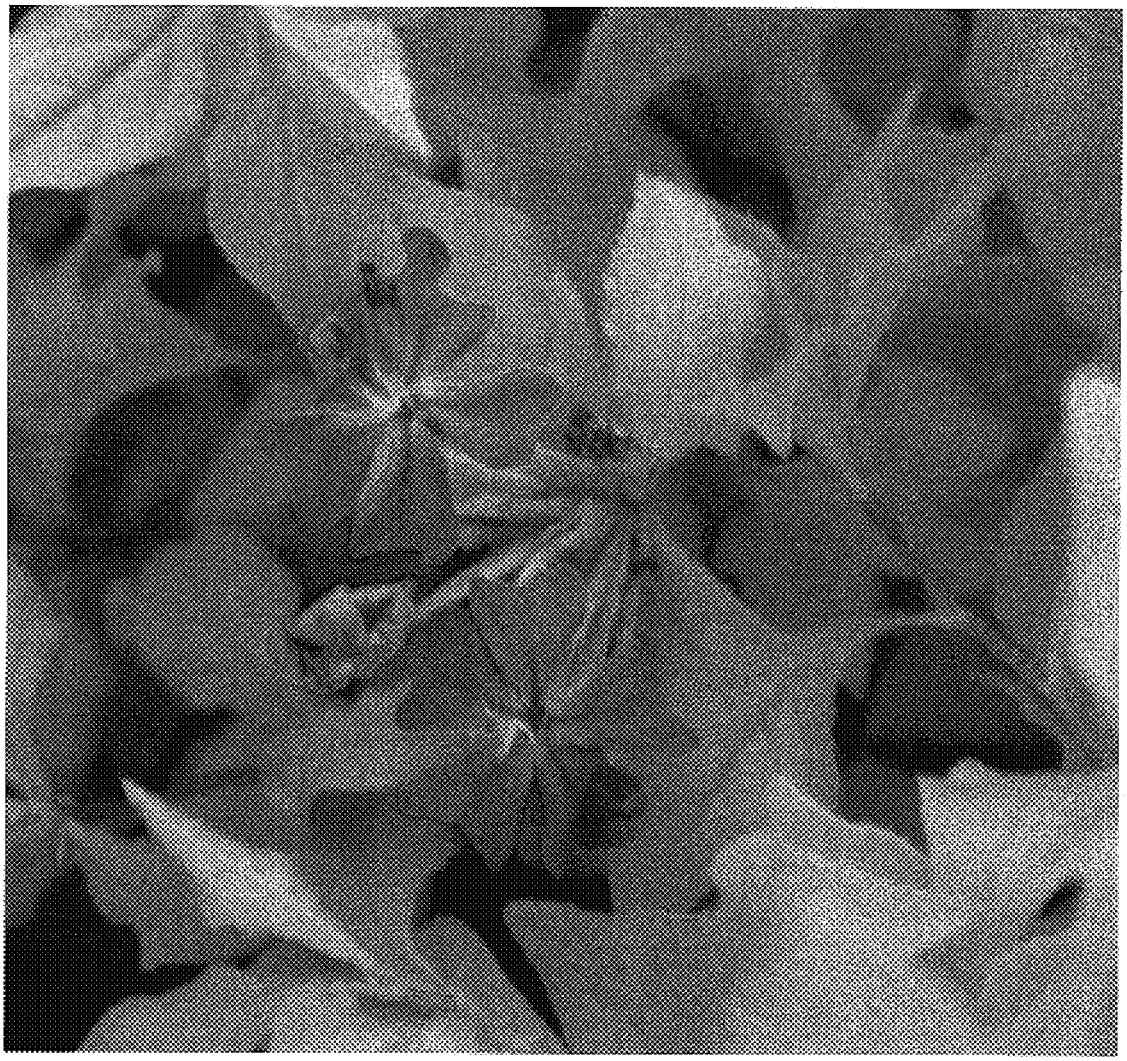
FIG. 2 depicts a close-up view of the flower.

All drawings were made using conventional techniques and although colors may appear different from actual colors due to light reflectance, they are as accurate as possible by conventional photography.

BOTANICAL DESCRIPTION OF THE PLANT

The following is a detailed botanical description of the new *Ceratostigma* cultivar named 'My Love'. Data was collected in Arroyo Grande, Calif. from plants grown out-of-doors in 1-liter containers. Color determinations are in accordance with The 2001 Royal Horticultural Society Colour Chart of London, England except where general color terms of ordinary dictionary significance are used. The growing requirements are similar to the species.

Botanical classification: *Ceratostigma willmottianum* 'My Love'.
Family: Plumbaginaceae.
Genus: *Ceratostigma.*
Species: *willmottianum.*
Denomination: 'My Love'.
Common name: Plumbago.
Plant use: Ornamental for use in container or small garden.
Parentage: *Ceratostigma willmottianum* 'My Love' is a seedling selection that resulted from the deliberate open cross-pollination of the following parents:
- *Female parent.*—An individual *Ceratostigma willmottianum* 'Forest Blue'.
- *Male parent.*—An individual *Ceratostigma willmottianum* 'Desert Skies'.

Type: Shrub.
Vigor: Vigorous.
Habit: Compact.
Dimensions (at one year): 23 cm in height and 30 cm in width.
Dimensions (at maturity): 30 cm. in height and 60 cm in width.
Hardiness: USDA Zone 7.
Asexual propagation: Semi-ripe cuttings.
Root system: Fine.
Cultural conditions: Full sun or partial shade, moderate to regular water, and fertile well-draining soil.
Time to initiate roots: 4–6 weeks.
Crop time: 4–8 months to produce a finished 1-liter container.
Disease or pest susceptibility: Susceptible to two spotted red spider mite.
Seasonal interest: Clear-blue flowers in summer, and intense golden-yellow foliage color spring, summer, and fall.
Stem:
- *Stem shape.*—Angular.
- *Internode length* (*average*).—1 cm.
- *Stem width.*—2 mm.
- *Stem length* (*average*).—12 cm.
- *Stem surface.*—Bristled.
- *Stem color.*—144A.

Foliage:
- *Foliage type.*—Winter deciduous.
- *Arrangement.*—Whorled.
- *Division.*—Simple.
- *Shape.*—Broadly oblanceolate.
- *Base.*—Attenuate.
- *Apex.*—Acute.
- *Venation.*—Pinnate.
- *Vein color* (*adaxial and abaxial surfaces*).—N144A.
- *Attachment.*—Sessile.
- *Stipules.*—Absent.
- *Margin.*—Entire and ciliate.
- *Length* (*range*).—2 cm to 2.75 cm.
- *Width* (*range*).—1 cm to 1.50 cm.
- *Leaf color* (*adaxial surface*).—153D.
- *Leaf color* (*abaxial surface*).—151D.
- *Leaf surfaces* (*adaxial and abaxial*).—Pubescent.
- *Foliar fragrance.*—None observed.

Flower:
- *Inflorescence form.*—Terminal spikelet.
- *Inflorescence width.*—6 cm.
- *Peduncle dimensions.*—0.40 cm in length and 2 mm in width.
- *Peduncle shape.*—Terete.
- *Flower shape.*—Rotate.
- *Flower quantity.*—9–12 flowers per inflorescence.
- *Lastingness of flower* (*on plant*).—Average of 2 days per flower.
- *Flower diameter.*—1.50 cm.
- *Flower depth.*—1.50 cm.
- *Flower aspect.*—Outward to upward.
- *Corolla tube diameter.*—2 mm.
- *Corolla tube length.*—0.75 cm.
- *Corolla tube shape.*—Terete.
- *Corolla tube surfaces* (*ventral and dorsal*).—Glabrous.
- *Corolla tube color.*—100D.
- *Petals.*—5 in number.
- *Petal shape.*—Obdeltoid.
- *Petal apex.*—Emarginate.
- *Petal base.*—Attenuate.
- *Petals fused or unfused.*—Fused.
- *Petal color* (*adaxial and abaxial surfaces*).—Ranges between N109B, N109C and 105D.
- *Petal surface* (*abaxial and abaxial*).—Glabrous.
- *Petal surface* (*adaxial*).—Glabrous.
- *Petal width.*—6 mm.
- *Petal margin.*—Entire.
- *Sepals.*—Five in number.
- *Sepal margin.*—Entire.
- *Sepal shape.*—Lanceolate.
- *Sepal surfaces* (*adaxial and abaxial*).—Pubescent.
- *Sepal dimensions.*—9 mm. in length and 3 mm. in width.
- *Fused or unfused.*—Sepals are overlapping.
- *Sepal apex.*—Aristate.
- *Blooming period.*—Summer.
- *Fragrance.*—None observed.

Reproductive organs:
- *Stamens.*—5 in number.
- *Stamen attachment.*—Basally fused.
- *Stamen color.*—155B.
- *Stamen dimensions.*—1 cm in length and <1 mm in width.
- *Anther attachment.*—Dorsifixed.
- *Anther dimensions.*—2 mm in length and <1 mm in width.

*Anther color.*—102A.
*Pollen color.*—104D.
*Pollen quantity.*—Moderate.
*Pistil.*—One.
*Pistil color.*—155B.
*Pistil dimensions.*—1.50 cm in length and <1 mm in width.
*Stigma.*—Forked filaments.
*Stigma color.*—155B.
*Stigma dimensions.*—1 mm in length and <1 mm in width.
*Style shape.*—Filament.
*Style color.*—155B.
*Style dimensions.*—1 cm in length and <1 mm in width.
*Seed.*—None observed to date.

What is claimed is:

1. A new and distinct variety of *Ceratostigma* plant named 'My Love' as described and illustrated herein.

* * * * *